(12) United States Patent
Navis

(10) Patent No.: US 6,589,212 B1
(45) Date of Patent: Jul. 8, 2003

(54) GUIDE FOR SURGICAL DEVICE

(75) Inventor: John A. Navis, Naperville, IL (US)

(73) Assignee: Janin Group, Inc., Naperville, IL (US)

( * ) Notice: Subject to any disclaimer, the term of this patent is extended or adjusted under 35 U.S.C. 154(b) by 0 days.

(21) Appl. No.: 09/436,118

(22) Filed: Nov. 8, 1999

(51) Int. Cl.⁷ ............................................ A61M 5/178
(52) U.S. Cl. .................................................. 604/164.01
(58) Field of Search ....................... 604/164.01–164.09, 604/164.11, 164.12, 158–163, 264, 523, 93.01

(56) References Cited

U.S. PATENT DOCUMENTS

| | | | |
|---|---|---|---|
| 3,877,429 A | * | 4/1975 | Rasumoff |
| 4,023,559 A | * | 5/1977 | Gaskell |
| 4,252,131 A | * | 2/1981 | Hon et al. |
| 4,498,902 A | | 2/1985 | Ash et al. |
| 4,581,025 A | * | 4/1986 | Timmermans |
| 4,596,559 A | * | 6/1986 | Fleischhacker ............. 604/170 |
| 4,921,479 A | | 5/1990 | Grayzel |
| 4,946,446 A | | 8/1990 | Vadher |
| 5,221,263 A | * | 6/1993 | Sinko et al. |
| 5,397,311 A | * | 3/1995 | Walker et al. ............... 604/160 |
| 5,501,670 A | * | 3/1996 | Sak ............................. 604/110 |

OTHER PUBLICATIONS

Medigroup, Inc. Peritoneoscopic Placement of Catheters, 11/97.

* cited by examiner

*Primary Examiner*—Brian L. Casler
*Assistant Examiner*—Ann Y. Lam
(74) *Attorney, Agent, or Firm*—Olson & Hierl, Ltd.

(57) ABSTRACT

The present invention comprises a surgical implement guide sized for insertion into and compatible with tissues. The invention includes a hollow shaft formed of a flexible material with memory to return to a predetermined configuration, where the shaft defines a central passageway of variable inside diameter and is adapted to receive a catheter or other surgical tool or instrument. The central passageway terminates in an access opening and allows for insertion and removal of the catheter or tool An elongated tab member having at least one surface or portion thereof which is textured extends from the shaft, and positioned adjacent the access opening, acting as a handle to assist the user in removing the catheter. A tip is included opposite the tab to assist in the insertion of the guide, and thus the catheter or tool.

48 Claims, 12 Drawing Sheets

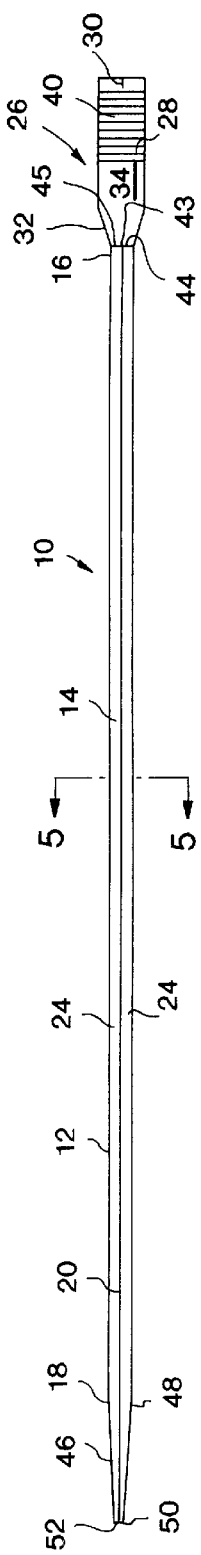
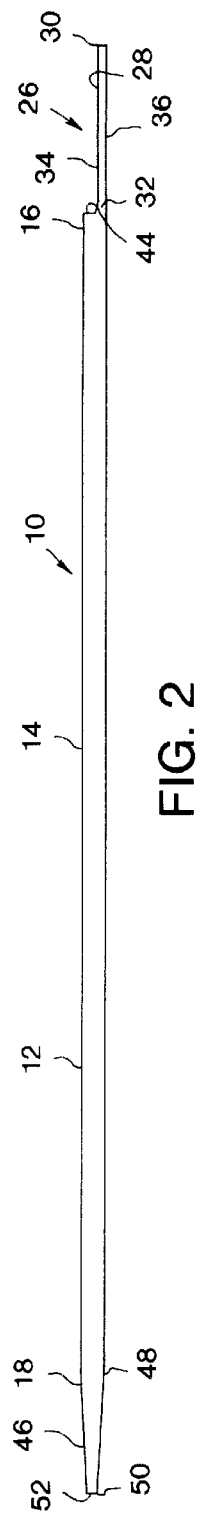
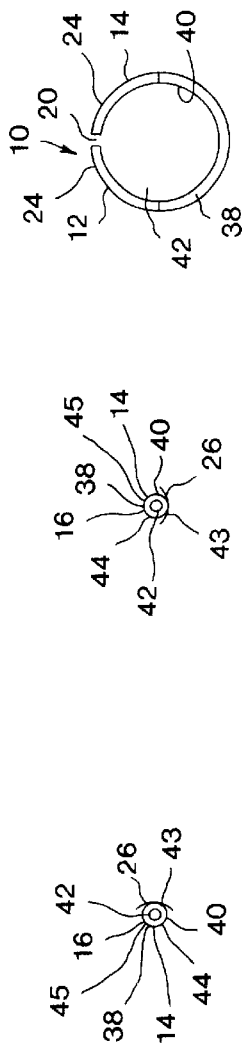
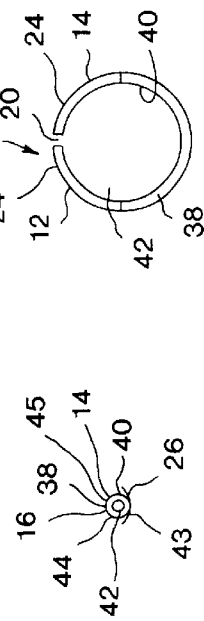
FIG. 1   FIG. 2   FIG. 3   FIG. 4   FIG. 5

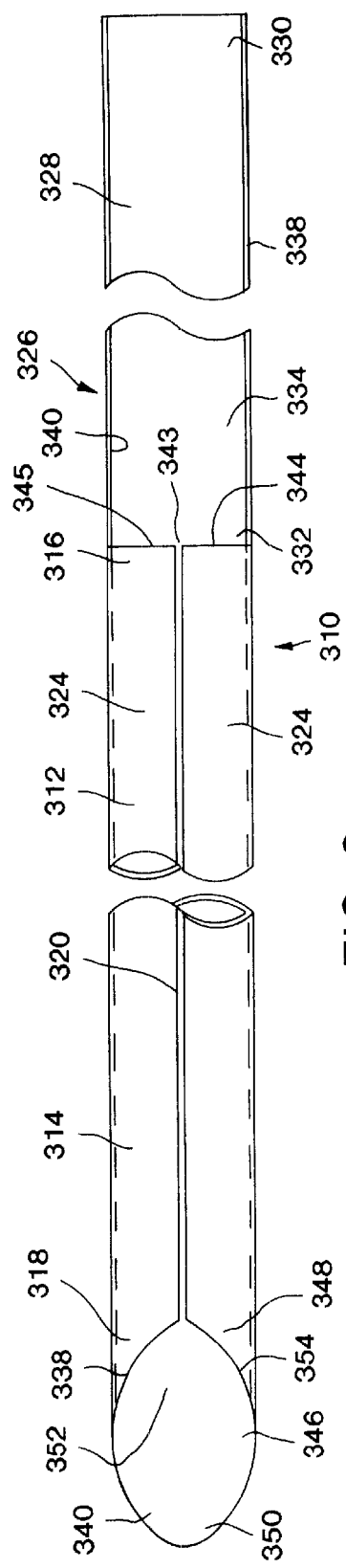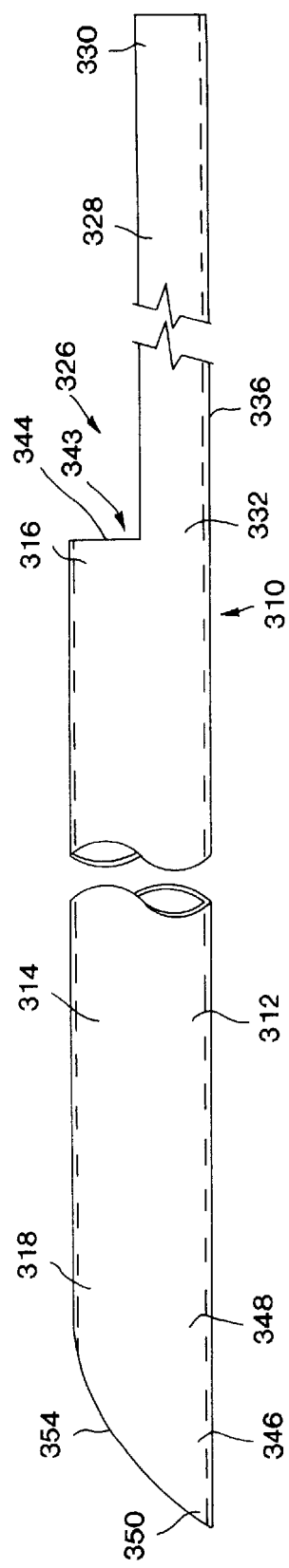

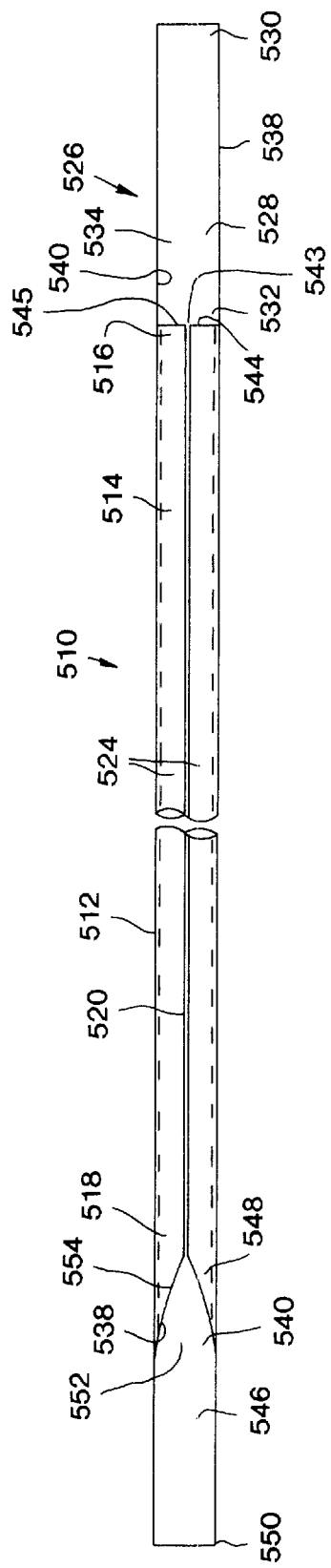
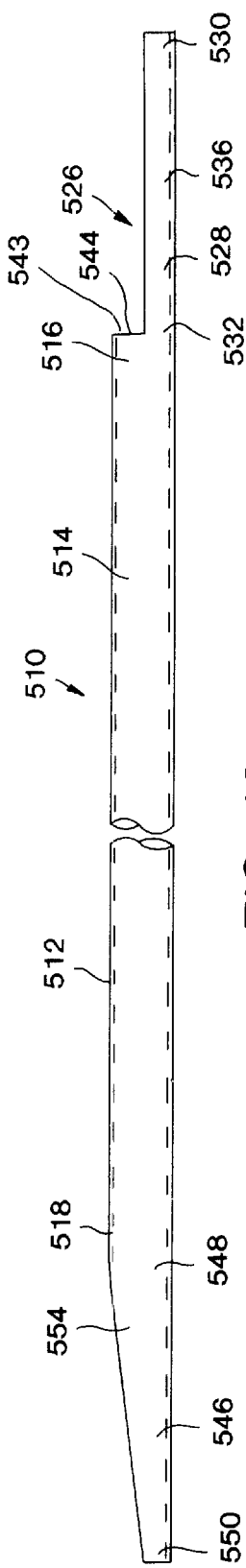

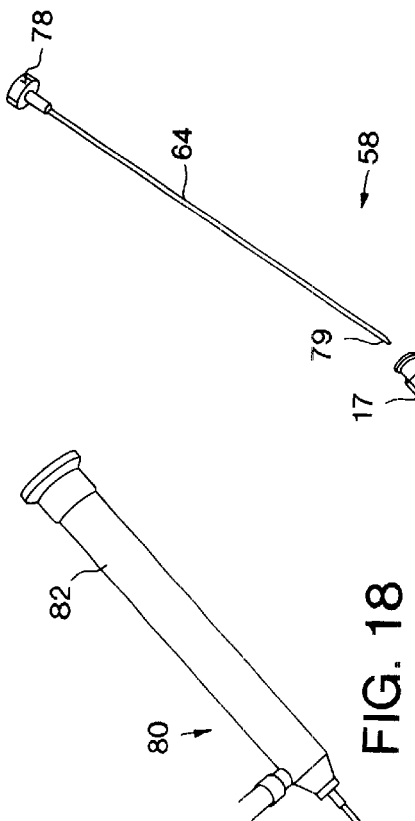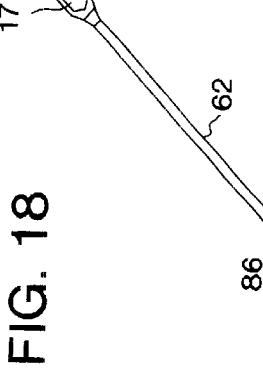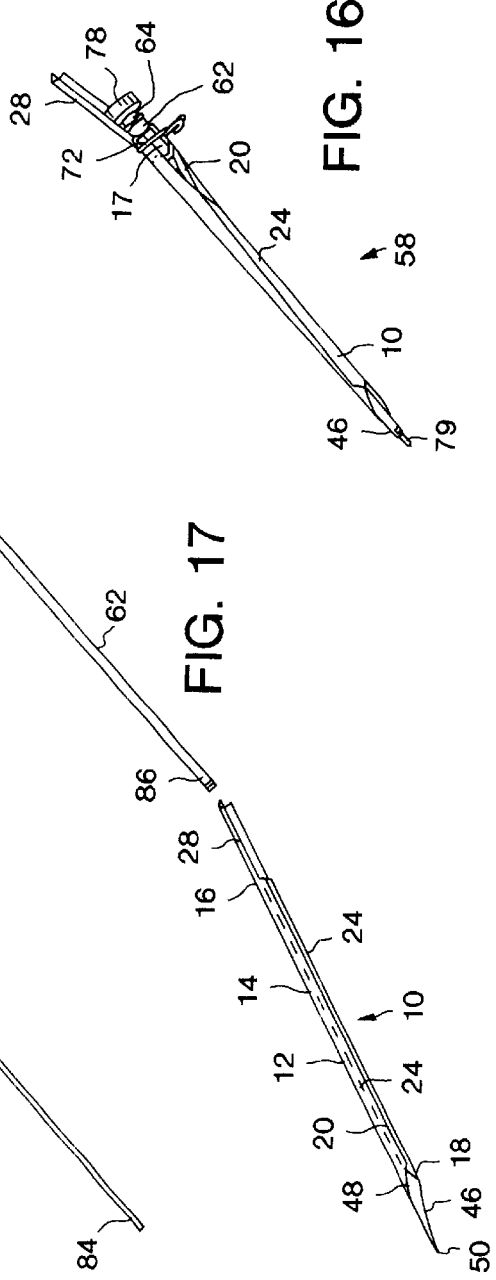

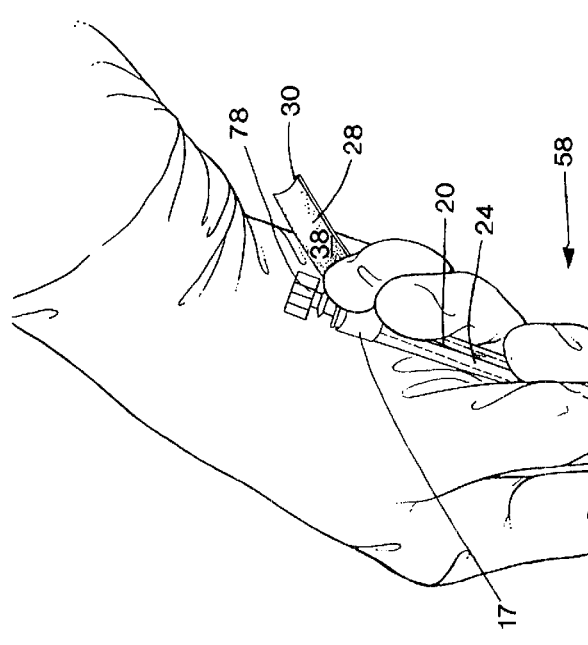
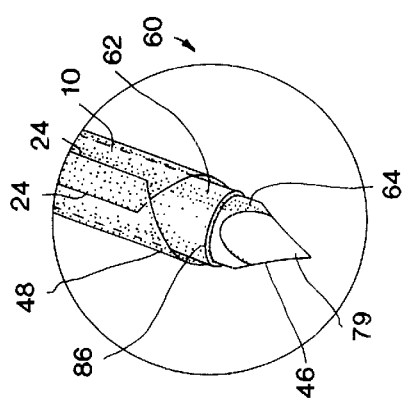
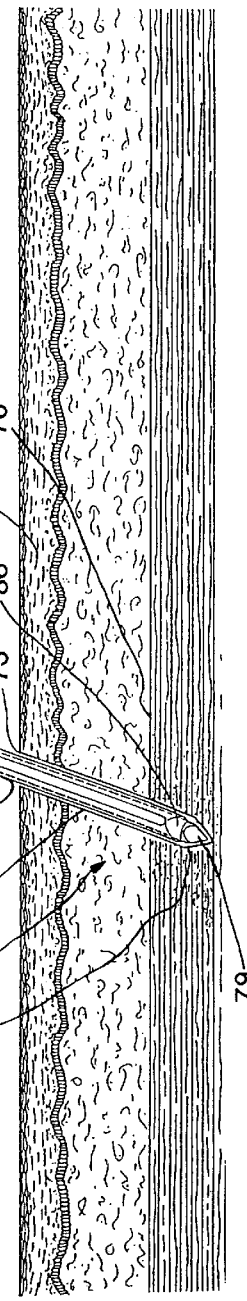
FIG. 20
FIG. 21

GUIDE FOR SURGICAL DEVICE

TECHNICAL FIELD OF THE INVENTION

This invention relates to a surgical implement guide and more particularly to a flexible guide used to percutaneously introduce a surgical instrument, including a cannula and a trocar, into or through various tissue.

BACKGROUND OF THE INVENTION

Peritoneal dialysis is a procedure in which a sterile glucose and salt solution is placed into the peritoneal cavity. The solution plus impurities are removed from the blood at some later time and fresh fluid is reinfused or the cycle can repeat itself. Peritoneal dialysis is effective for treatment of kidney failure and has been used for more than 30 years for this purpose.

One of the most successful devices used for peritoneal dialysis is the Tenckhoff catheter developed in the mid 1960's. This catheter is a silicon rubber tube with numerous drainage holes on its inner portion. Generally, the catheter has two polyester (e.g. Dacron$^R$) "cuffs" which are respectively placed in the subcutaneous tissue and the muscle layer of the patient. These cuffs serve to limit peritoneal leakage, minimize infection and enclose the catheter in the body. The issue arises in the placement of the catheter.

Likewise, insertion of catheters into blood vessels is frequently accomplished percutaneously, where a needle with a guide wire is used to initially enter the vessel, rather than use a surgical cut-down procedure. Early procedures used the puncture needle itself as the direct conduit into the abdomen or a blood vessel for a catheter of sufficiently small diameter.

Subsequent art first developed metal sheaths and/or trocars that were formed with a slot, or were split into two distinct pieces for subsequent removal. Rapid development in the art substituted thin-walled plastic sheaths, or other suitable material, for the metal sheaths. The most common such prior art sheath is generally known as a "split sheath". It consists of a cylindrical sheath which, at the distal end is formed to taper to a small diameter opening to permit insertion of a guide wire. The opposing proximal end typically has two handles or finger stops formed on opposing sides of the sheath. Score marks are formed along the full length of the sheath and are designed to cause the guide to split apart when the handles are pulled, facilitating the removal of the guide from the body.

The process of implanting a catheter with this type of split sheath is called the Seldinger Technique. Specifically, in this technique a needle is inserted into a blood vessel. A stainless steel braided wire is then inserted through the needle into the blood vessel, and then the needle is retracted.

The catheter is inserted into the sheath and the opposite or trailing edge of the wire is inserted into the distal opening of the sheath. The wire is pushed through the distal end of the catheter and out the proximal end. Then the sheath with the catheter is pushed into the blood vessel, using the wire as a guide. The cone-shaped end of the guide/sheath enters the vessel wall so that the main body of the sheath can be inserted into the blood vessel. After the majority of the sheath, preferably between about 75% to about 80%, is inserted into the vessel, the wire is removed by pulling it out through the sheath tip.

The physician then grasps the handles and simultaneously pulls them apart one from the other, causing the sheath to split. While the sheath is being split, it is simultaneously retracted from the blood vessel. It should be noted that retracting the sheath may cause the catheter to be inadvertently retracted during this step. If so, then the catheter must be advanced again back to its original position. The same procedure is utilized to gain access to the peritoneal region.

The process of splitting, retracting, and readvancing is repeated as necessary until the sheath is totally removed, and the catheter fully and accurately positioned. If the catheter does inadvertently come out at any point during the process, the entire process must be repeated, beginning with the insertion of the needle.

Generally, during the process, the sheath becomes covered in fluid, making it difficult to grasp. Thus, the above discussed sheaths have a disadvantage in that both hands must be employed to remove the sheath, leaving the catheter unattended, unless an assistant is present. In some instances, it was found that pulling on the sheath caused it to tear prematurely. Another example of a split sheath is disclosed in Y.TEC's Peritoneoscopic Placement of Peritoneal Dialysis Catheters. This sheath attempts to solve some of the disadvantages of the prior art, displaying a guide with a tip and a substantially flat tab. The tab is substantially flat and smooth and can be difficult to grab when it becomes covered in fluid. Again, both hands must be employed, or some other device, such as a hemostat, must be used.

Another disadvantage is that such prior art sheaths tend to be of a predetermined specific diameter which is not adjustable. These sheaths generally don't provide alternatives, nor are they adaptable to accommodate different types of catheters, trocars, or instruments, or even patient situations.

SUMMARY OF THE INVENTION

The present invention provides a device which overcomes the above discussed problems using a surgical implement guide sized for insertion into tissue. The guide includes a shaft formed of a flexible material with memory to return to a predetermined configuration, or with ability to have a new or different memory set into it, an opening and passage way of infinitely adjustable dimensions between a predetermined minimum and maximum dimension extendable through the entire length of the shaft and an elongated tab member having at least one textured surface extending from the shaft that acts as a handle for placing, removing or controlling the guide.

In particular, the present invention comprises a surgical implement guide sized for insertion into tissue and a surgical assembly employing the guide. The guide includes a shaft formed of a flexible material with memory to return to its predetermined configuration. The shaft is adapted to receive a catheter in a chamber defined in the shaft. Moreover, the shaft includes an elongated tab member, preferably a tab integral with the shaft, extending from the shaft that is used as a handle to both place, control and remove the guide.

The guide further includes an opening and passageway of adjustable dimensions as well as a tip portion for the shaft. Preferably the tip is integral with the shaft. The passageway preferably extends axially the entire length of the shaft, although some lesser distance can be utilized depending on the application as long as it allows for removal of the catheter. The tip is situated opposite the elongated tab member. The tip configuration can vary and is selected to assist in the insertion of the guide.

The guide may have many different forms to accommodate different surgical instruments, surgical procedures, patients or surgeons. The tab member can be integral with the shaft or joined thereto, and have a width substantially equal to or less than an outer circumference of the shaft. The tab can be substantially flat, curved or pointed in relation to the shaft and rectangular, angled or curved in shape. Moreover, the guide and the tab can have at least one smooth surface and one textured surface, or portion thereof, or two textured surfaces or portions thereof.

Likewise, the tip and shaft configurations can vary depending on the application. The tip can have an outer diameter substantially equal to or less than the outer diameter of the shaft, so that the tip is pointed, blunted, round, angled or even curved in some fashion. Furthermore, the shaft's outer diameter can be substantially the same over its entire length, so that it is substantially cylindrical in shape, or it can vary over the length of the shaft so that it is substantially conical or truncated in shape.

Numerous other advantages and features of the present invention will become readily apparent from the following detailed description and from the accompanying drawings.

BRIEF DESCRIPTION OF THE DRAWINGS

In the drawings,

FIG. 1 is a top plan view of a surgical implement guide in accordance with the present invention;

FIG. 2 is a side elevational view of the surgical implement guide of FIG. 1;

FIG. 3 is an end view of the surgical implement guide of FIG. 1;

FIG. 4 is an end view of the surgical implement guide of FIG. 2;

FIG. 5 is a cross-sectional view of the surgical implement guide of FIG. 1 taken substantially along line 5—5;

FIG. 8 is a top plan view of second alternate embodiment of the surgical implement guide of FIG. 1;

FIG. 9 is a side elevational view of the second alternate embodiment of the surgical implement guide of FIG. 8;

FIG. 12 is a top plan view of fourth alternate embodiment of the surgical implement guide of FIG. 1;

FIG. 13 is a side elevational view of the fourth alternate embodiment of the surgical implement guide of FIG. 12;

FIG. 16 is a perspective view of the surgical implement assembly including the trocar in accordance with the present invention;

FIG. 17 is an exploded view of the assembly of FIG. 16 depicting the guide and trocar with the obturator removed from the cannula;

FIG. 18 is a perspective view of the scope used with the cannula;

FIG. 20 is an enlarged partial view of the tip of the guide, with the tip secured by the trocar;

FIG. 21 a schematic representation of the assembly of FIG. 16 being used on a patient;

DESCRIPTION OF THE PREFERRED EMBODIMENT

Figure 6:
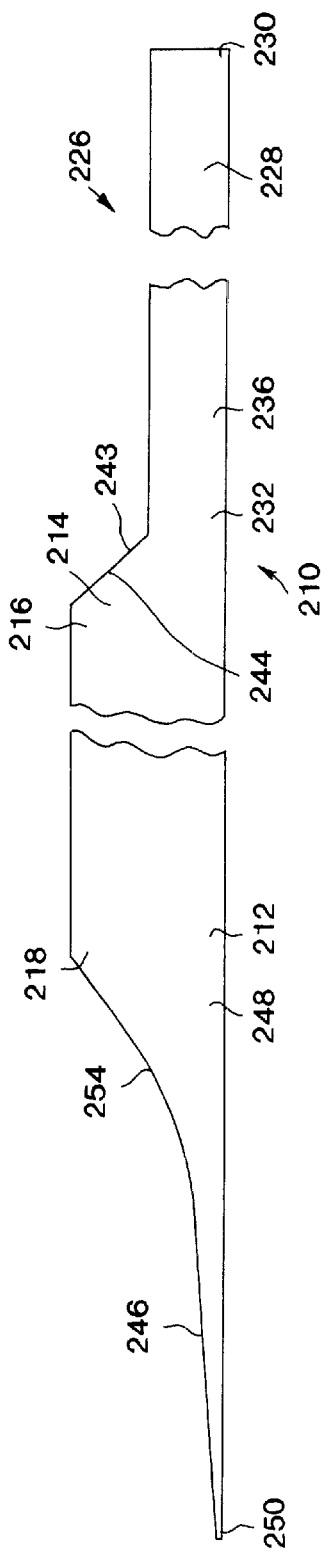
FIG. 6 is a side elevational view of a first alternate embodiment of the surgical implement guide of FIG. 1.

Turning now to FIGS. 1 and 2, a surgical implement guide, generally designated 10, is shown sized for percutaneous insertion into tissue in accordance with the present invention. As shown in FIGS. 1 and 2, guide 10 includes an elongated shaft 12 formed of a flexible material with memory to return to an original configuration. Any suitable material, such as biocompatible polyurethane, is contemplated. In one preferred embodiment, shaft 12 is comprised of polypropylene or other similar material, and may either be clear, opaque or tinted.

It is contemplated that guide 10 could be of any length, however it is preferred that guide 10 be between about 4 inches and about 24 inches long, where shaft 12 is preferably between about 1 inch and about 22 inches in length. Shaft 12 is shown with an outer surface 14 and opposed proximal and distal ends 16 and 18, where it is contemplated that proximal end 16 is straight or flared, and where shaft 12 is adapted to receive a catheter (not shown) or other suitable device in a passageway defined therein (best illustrated in FIG. 5).

An opening or slot 20 is defined in shaft 12, to allow for expansion and compression of the guide 10 and to allow for insertion and removal of the catheter into and from the body. As provided above, shaft 12 is formed of a flexible material allowing opposing sides 24 of shaft 12 to slidably pass one over the other so that the guide 10 may be "rolled" into a diameter slightly smaller than its normal diameter prior to insertion into tissue. As guide 10 is formed of a material with memory to return to its original configuration, guide 10 will be biased to return to its original shape.

The dimensions of slot 20 are adjustable depending on the length of the shaft 12, so that slot 20 is extendable through the entire length thereof. In one preferred embodiment, slot 20 axially extends from proximal end 16 to distal end 20 as shown in FIG. 1, providing for easy insertion and removal of the catheter. However, it is also contemplated that slot 20 may not extend the entire length of the shaft 12, but extend some lesser distance. Moreover, end 16 can be straight or flared to accommodate and/or encapsulate the catheter.

Moreover, it is contemplated that shaft 12 can have more than one slot 20, preferably parallel to each other, although other arrangements are contemplated, which are used to position the guide 10, place the catheter, or position tools used to place the catheter.

An elongated tab member 26 extends from proximal end 16 of shaft 12, where the elongated member 26 acts as a tab or handle, providing a sure grip for the user during insertion or withdrawal of the guide 10, or removal of the catheter therefrom. As depicted, elongated member 26 is a tab 28 joined to shaft 12 at proximal end 16, in one preferred embodiment, tab 28 is formed integral with shaft 12.

FIG. 1 illustrates a tab 28 which is substantially rectangular in shape, having proximal and distal ends 30 and 32 respectively, where distal end 32 is connected to, and preferably integral with, proximal end 16. While a rectangular embodiment is depicted for tab 28, many shapes are contemplated, including an angled or curved tab. Tab 28 could further be formed with a blunt proximal end 30 suitable to push the guide 10 into the tissue, or tab 28 could be flared to accommodate and encapsulate various hubs, knobs, etc.

It is further contemplated that tab 28 is substantially curved or flat depending on the application. In one embodiment, depicted in FIGS. 1 and 2, tab 28 has a width less than the outer circumference of the shaft 12, so that tab 28 is substantially flat (best seen in FIGS. 3 and 4). While tab 28 has a slight curve when viewed from the end, it is substantially flat in relation to shaft 12. Moreover, other embodiments are contemplated in which tab 28 has a width substantially equal to the outer circumference of shaft 12.

Tab 28 is formed with two surfaces, first and second surfaces 34 and 36 respectively. As provided above, tab 28 acts as a handle, providing a sure grip for the user during insertion or withdrawal of the guide 10, or removal of the catheter therefrom. Therefore, it is contemplated that tab 28 has at least one surface with a texture on all or portion thereof, first surface 34 for example (or second surface 36), which would provide a non-slip surface to assure a good grip. In this instance, the other surface, second surface 36 would be smooth. Alternatively, it is contemplated that all or a portion of first and second surfaces 34, 36 could be textured, or that first surface 34, for example, could be texture and only a portion of second surface 36 textured, all to provide a good gripping surface.

Turning to FIGS. 3–5, more detail is provided on the chamber. FIGS. 3 and 4 depict an end view of the guide 10 of FIGS. 1 and 2, respectively. In addition to the outside surface 14, shaft 12 includes a shaft wall 38, with an inner surface 40 defining passageway or chamber 42. In the preferred embodiment, outer surface 14 is merged with, and is integral with, second surface 36 while inner surface 40 merges with first surface 34. Additionally, guide 10 includes a first opening 43 defined by edges 44 and 45 at proximal end 16. Edges 44 and 45 provide a convenient abutment which coacts with the instrument or catheter within the guide 10. This arrangement provides visual confirmation of the encapsulation of the instrument or catheter.

FIG. 5 is a cross-sectional view of the guide 10 of FIG. 1 taken substantially along line 5—5 thereof. FIG. 5 reveals that slot 20 is formed in shaft wall 38 of shaft 12 and in fluid communication with chamber 42. In this manner, a catheter can be passed through slot 20 into chamber 42 and retained therein. FIG. 5 further reveals that shaft 12 can be rolled into the smaller diameter so that opposing sides 24 slidingly pass one over the other.

Turning back to FIGS. 1 and 2, it will be appreciated that guide 10 further includes a tip 46 having proximal and distal ends 48 and 50, located opposite tab 28 at shaft distal end 18. While it is understood that tip 46 can be joined to guide 12 by bonding, gluing or the like, it is preferred that tip 46 is integral with guide 12. Moreover, it is preferred that slot 20 could extend through tip 46 into, and in fluid communication with, tip opening 52 defined at tip distal end 50, where tip opening 52 is in fluid communication with chamber 42. However, it is also contemplated that slot 20 could terminate proximate shaft distal end 18 as discussed above.

As evidenced by the FIGURES, it is contemplated that tip 46 could have a large variety of configurations depending on the application. It is also contemplated that tip 46 could be designed so that it fits snugly around or fully encloses the catheter.

As provided above, tip 46 can be pointed, rounded, angled or blunted depending on the application. In one embodiment, it is contemplated that tip 46 has an outer diameter substantially equal to an outer diameter of shaft 12, so that shaft 12 and tip 46 are substantially cylindrical in shape. However, in the preferred embodiment tip 46, as shown in FIGS. 1 and 2, has an outer diameter less than the outer diameter of shaft 12 so that tip 46 is pointed, even tapering to a virtually closed point, to allow easy insertion into the tissue or bent in towards the chamber 42 as shown in FIG. 16. Tip 46 could also have a smaller outer diameter than shaft 12 and yet not be as pointed as depicted, i.e., tip 46 could be angled, blunted or rounded.

Similarly, it is contemplated that shaft 12 could have many configurations depending on the application. In one embodiment, as depicted in FIGS. 1 and 2, it is contemplated that the outer diameter of shaft 12 is substantially the same over its entire length, so that shaft 12 is substantially cylindrical in shape. However, it is also contemplated that the outer diameter of shaft 12 varies over the length of the shaft 12. For example, the outer diameter of shaft 12 at proximal end 16 could be greater than the outer diameter at distal end 18 so that shaft 12 is substantially conical or truncated.

Figure 7:
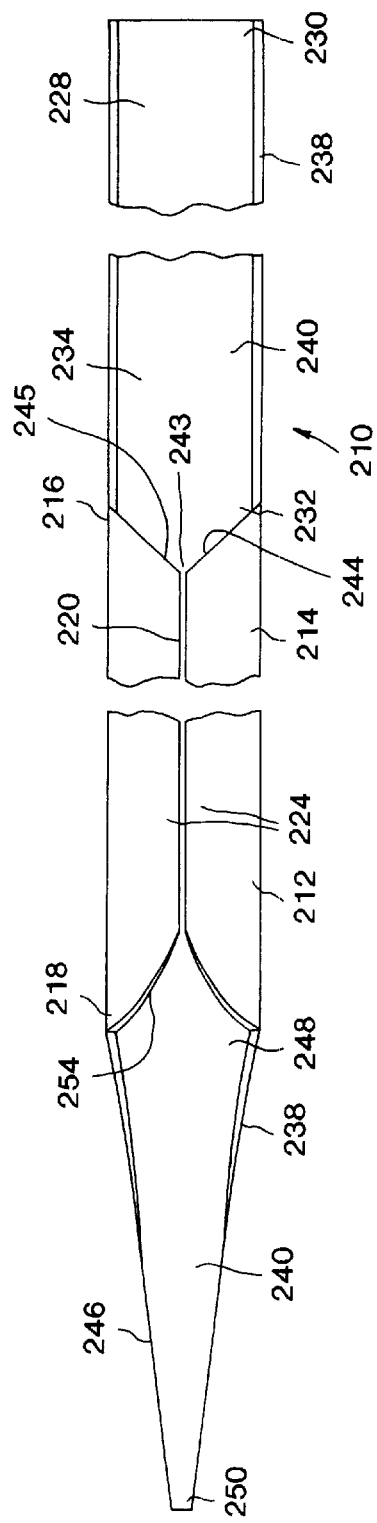
FIG. 7 is a top plan view of the surgical implement guide of FIG. 6.

Turning now to FIGS. 6 and 7, an alternate embodiment of the guide 10 of FIGS. 1–5 is depicted. Correspondingly, where appropriate, the last two digits in the 200 series of numerals depicted in FIGS. 6 and 7 are connected to elements which have the same function and/or structure as those described with regard to FIGS. 1–5.

FIGS. 6 and 7 depict a guide 210 similar to guide 10 of FIGS. 1 and 2, however tip 246 and tab 228 differ from tip 46 and tab 28. As depicted, tab 228 is shown with tab proximal end 230 having a more blunted appearance (best seen in FIG. 7) than proximal end 30 (best seen in FIG. 2) providing a better holding surface for pushing guide 210 into the tissue when compared with guide 10. Additionally, tab distal end 232 has a more blunted or squared appearance when compared to the distal end 32.

Tip 246 also differs from tip 46. Tip 246 is not as pointed as tip 46, instead tip 246 has a blunted distal end 250 in addition to a concave transition portion 254 which is in communication with both proximal and distal ends 248 and 250. Transition portion 254, in combination with slot 220, provides for easier insertion of the guide into the body. The bevel formed by converging edges 243 accommodates manufacturing tolerance variations.

Like guide 10, guide 210 is formed so that first opening 343 is defined by edges 244 and 245 in fluid communication with chamber 242. Edges 244 and 245 also provide a convenient abutment which coacts with the instrument or catheter within the guide 210. Again, this arrangement provides visual confirmation of the encapsulation of the instrument or catheter.

Yet another alternate embodiment of the present invention is revealed in FIGS. 8 and 9. Correspondingly, where appropriate, the last two digits in the 300 series of numerals depicted in FIGS. 8 and 9 are connected to elements which have the same function and/or structure as those described with regard to FIGS. 1–7.

FIGS. 8 and 9 depict a guide 310 similar to guide 10 and 210 of FIGS. 1, 2, 6 and 7, however here again tip 346 is different. As depicted, tab 328 is shown with tab proximal end 330 having a blunted appearance (best seen in FIG. 9) than distal end 30 (best seen in FIG. 2) providing a better surface for holding guide 310 in the tissue when compared with guide 10. Additionally, tab distal end 332 has a more blunted or squared appearance when compared to the distal end 32. Edges 344 and 345 define opening 343 and provide an abutment similar to that provided by edges 44 and 45 shown in FIG. 1.

Tip 346 also differs from tips 46 and 246. Tip 346 is not as pointed as tip 46, instead tip 346 has a more angled appearance in addition to having a convex transition portion 354 which is in communication with both proximal and distal ends 348 and 350. As shown in FIGS. 8 and 9, tip opening 352 is larger than tip opening 52 but smaller than tip opening 252. Tip opening 352, in combination with transition portion 354 and slot 320, provides for easy insertion of the guide.

Figure 10:
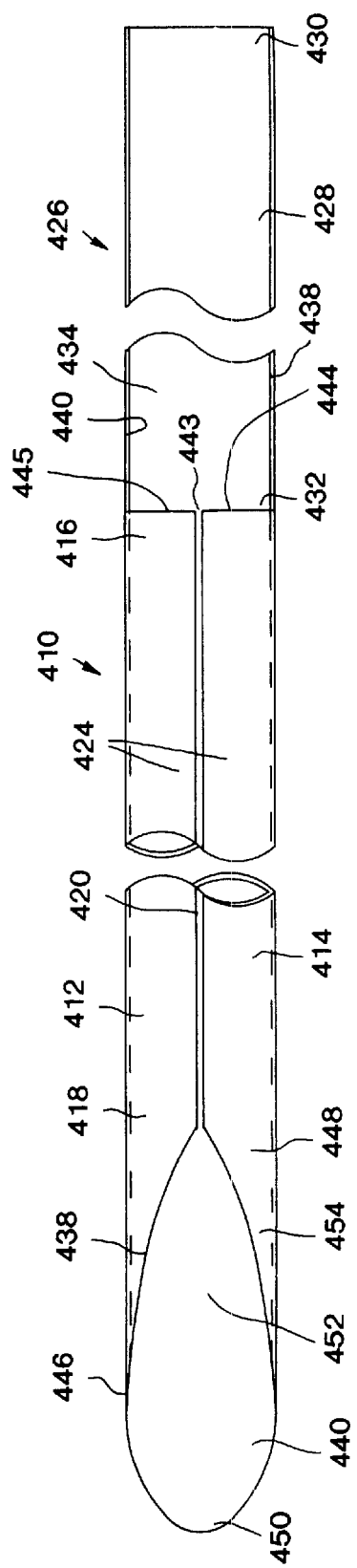
FIG. 10 is a top plan view of third alternate embodiment of the surgical implement guide of FIG. 1.
Figure 11:
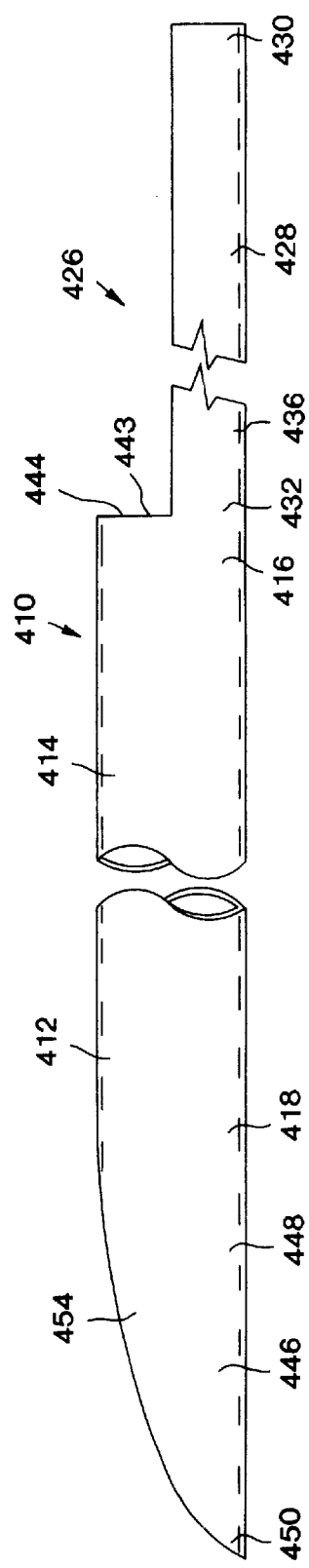
FIG. 11 is a side elevational view of the third alternate embodiment of the surgical implement guide of FIG. 10.

FIGS. 10 and 11 depict a third alternate embodiment of the present invention similarly to the guide 310 of FIGS. 8 and 9. Correspondingly, where appropriate, the last two digits in the 400 series of numerals depicted in FIGS. 10 and 11 are connected to elements which have the same function and/or structure as those described with regard to FIGS. 1–9.

FIGS. 10 and 11 depict a guide 410 with tab 426 and similar to guide 310 of FIGS. 8 and 9, however again tip 446 is different, having a more angled convex transition portion and larger tip opening 452. Edges 444 and 445 provide an abutment which coacts with the instrument or catheter within the guide similar to edges 44 and 45. As shown in FIGS. 10 and 11, tip opening 452 is larger than tip opening 52 and 352 but smaller than tip opening 252. Tip opening 452, in combination with transition portion 454 and slot 420, provides for easy insertion of the guide 410. It is also contemplated that tip 446 could be designed so that it fits snugly around or fully encloses the catheter.

Turning now to FIGS. 12 and 13 yet another alternate embodiment of the present invention is revealed. Correspondingly, where appropriate, the last two digits in the 500 series of numerals depicted in FIGS. 12 and 13 are connected to elements which have the same function and/or structure as those described with regard to FIGS. 1–11.

FIGS. 12 and 13 depict a guide 510 with tab 526 similar to guides 10, 210, 310 and 410 above, however again tip 546 differs. As depicted, tab 528 is shown with tab proximal end 530 having a blunted appearance (best seen in FIG. 13) than distal end 30 (best seen in FIG. 2) providing a better surface for holding guide 510 in the tissue when compared with guide 10. Additionally, tab distal end 532 has a more blunted or squared appearance when compared to the distal end 32. Edges 544 and 545 also define opening 543 and provide an abutment which coacts with the instrument or catheter within the guide 510 similar to the edges discussed above.

Tip 546 also differs from tips 46, 246, 346 and 446. Tip 546 has squared, blunted appearance with a blunted tip distal end 550, in addition to an angled transition portion 554. As shown in FIGS. 12 and 13, tip opening 552 is larger than tip opening 52 but smaller than tip opening 252. In fact, tip opening 552 is approximately equal to tip opening 452. Tip opening 552, in combination with transition portion 554 and slot 520, provides for easy insertion of the guide when compared to guide 10. It is further contemplated that tip 546 could be designed so that it fits snugly around or fully encloses the catheter.

Figure 14:
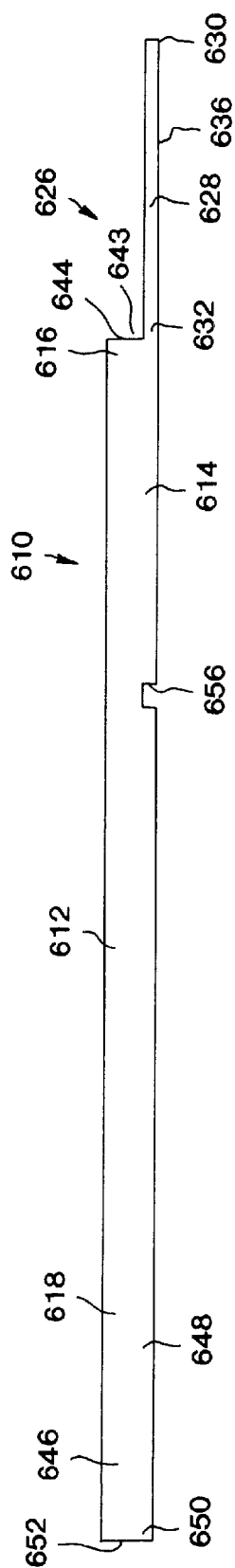
FIG. 14 is a side elevational view of fifth alternate embodiment of the surgical implement guide of FIG. 1.
Figure 15:
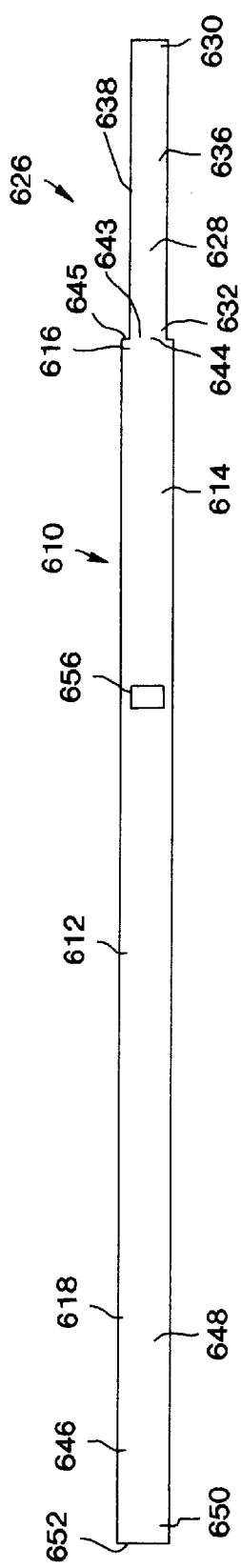
FIG. 15 is a bottom plan view of the fifth alternate embodiment of the surgical implement guide of FIG. 14.
Figure 19:
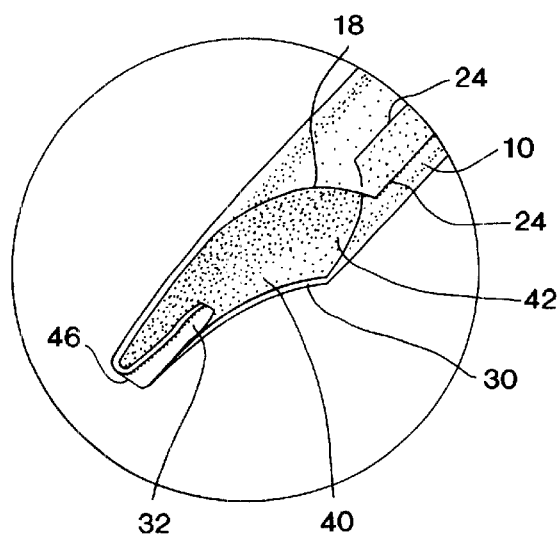
FIG. 19 is an enlarged partial view of the tip of the guide, with the tip turned in towards the chamber.

FIGS. 14 and 15 reveal yet one more alternate embodiment of the present invention. Correspondingly, where appropriate, the last two digits in the 600 series of numerals depicted in FIGS. 14 and 15 are connected to elements which have the same function and/or structure as those described with regard to FIGS. 1–13.

FIGS. 14 and 15 depict guide 610 with tab 626 which is similar to the guides discussed above. In this particular embodiment, edges 644 and 645 also provide visual confirmation of the encapsulated instrument or catheter. Further, in this embodiment, again tip 646 is different. As depicted, tab 628 is shown with tab proximal end 630 having a more blunted appearance (best seen in FIG. 14) than distal end 30 (best seen in FIG. 2) but not as blunt as tab proximal ends 230, 330, 430 and 530. Yet tab proximal end 630 still provides a good surface for holding guide 610 in the tissue. Additionally, tab distal end 632 has a more blunted or squared appearance when compared to the distal end 32. In this particular embodiment, edges 644 and 645 define opening 643 at proximal end 616. Edges 644 and 645 provide as abutment which coacts with the instrument or catheter within the guide 610, that provides visual confirmation of the encapsulation of the instrument or catheter.

Tip 646 also differs from tips 46, 246, 346, 446 and 546. Tip 646 has round appearance with a rounded tip distal end 650. In this embodiment, tip 646 portion has an outer diameter substantially equal to an outer diameter of the shaft 612, so that guide 610 has a cylindrical appearance. Again, as shown in FIGS. 14 and 15, tip opening 652 is larger than tip opening 52 but smaller than tip opening 252. As discussed above, tip opening 652, in combination with slot 620, is sized to accommodate various sizes and types of catheters, instruments and tools.

In addition to the above, guide 610 includes at least one notch 656 defined by wall 638 in shaft 612. While only one notch 656 is depicted, two or more notches 656 are contemplated. For some applications notch 656 can be omitted, if desired. It is contemplated that notch 656 has many uses, including being used for measuring increments or for attaching to or aligning with other surgical tools to help implant the catheter. However, in a preferred embodiment, it is contemplated that notch 656 is used to position the guide 610 relative to other surgical tools.

Turning now to FIGS. 16–28, a method of implanting a catheter, preferably a flexible catheter, or other device is shown. FIGS. 16 and 17 depict a surgical implement assembly 58 sized for insertion into a tissue, where the assembly includes a trocar 60, with a cannula 62 and obturator 64, received within guide 10. While guide 10 is referred to, this discussion of the assembly 58 is generally applicable to any of the guides 210, 310, 410, 510 and 610 provided above.

Operably connecting the guide 10 to trocar 60, specifically to cannula 62, assists the user in placing the guide. It is contemplated that trocar 60 or cannula 62 is operably assembled with the guide 10 in any number of ways. In the embodiment depicted in FIG. 16, a clip 72 compressedly urges guide 10 against cannula hub 17, to secure the guide 10 thereto and assist the user in proper placement thereof. In one preferred embodiment, it is contemplated that hub 17 has a groove formed therein for receiving clip 72. The groove assures proper placement of the clip 72 and good compressed contact.

In addition to clip 72, it is contemplated that other means could be used to operably connect the guide 10 and cannula 62. For example, guide 10 is operably connected to cannula 62 by adhesive tape, (not shown), where the adhesive tape is wrapped around guide 10 and compressedly urges guide 10 against cannula hub 17. Additionally, it is contemplated that an adhesive is provided on hub 17 so that the adhesive removably bonds the guide 10 to the cannula 62. Additionally, guide 10 can be removably joined to cannula 62 by a temporary heat bond.

The method of using the assembly 58, including the guide 10, is better understood by reviewing FIGS. 16–27. Preferably, the guide 10 is "rolled" into a diameter slightly smaller than its normal diameter prior to insertion and operably connected to the trocar 60, preferably to cannula 62, either using the means discussed above, or by fitting the guide 10 tightly to the cannula 62, so that tip 46 is mechanically interlocked with cannula 62 (best seen in FIGS. 19 and 20).

The patient's skin is anesthetized over the desired location in a vertical or horizontal direction for about 3 cm. The skin is then incised with a scalpel, creating about a 2–3 cm long primary incision forming entry point 73. A closed hemostat is inserted through the incision until the tip meets the resistance of the external fascia of the abdominal wall, where upon the hemostat is opened and withdrawn. A needle, preferably a 21-gauge needle, is inserted through the skin to anesthetize the abdominal wall, directing the needle towards the coccyx.

The assembly 58 including the trocar 60, consisting of the obturator 64 and cannula 62 shown in FIGS. 16 and 17, are removed from their packing with the obturator 64 firmly seated in the cannula 62 so that knob 78 of the obturator 64 opposite pointed tip 79 is fully exposed outside of the cannula 62. The assembly 58 is held so that the knob 78 of the obturator 64 is seated in the palm of the hand, with the operator's first finger placed at the middle on the assembly 58 pointing to the tip 46. The assembly 58 is inserted into the entry point 73 at a predetermined angle, preferably between about 20° to about 30° from vertical towards the coccyx, best seen in FIG. 21.

The assembly 58 is advanced through the subcutaneous tissue 74 and abdominal musculature 76 using a slight twisting/rotating motion in a direction towards the coccyx. Two "pops" should be discerned. Approximately half of the assembly 58 will pass through the skin while at least pointed tip 79 and tip 46 enters the peritoneum.

The obturator 64 is removed from the trocar 60 and a scope 80, consisting of a viewing portion 82 and tip 84 as shown in FIG. 18, is fully inserted into the cannula 62. It is important that the scope 80 and cannula 62 be fully locked together. Initially very bright white, but occasionally red, blood vessels may be seen when viewed through viewing portion 82 of the scope 80. Typically tip 84 is in contact with the visceral peritoneum and fixed in stationary position. The assembly 58 and scope 80 is withdrawn in 1 mm increments. At this time, a sweeping cranial-coccyxid movement of visceral surface should be viewed, which is one indication that the assembly 58 is in the correct intraperitoneal position.

After confirming the intraperitoneal space, the scope 80 and cannula 62 are advanced slightly. The scope 80 is removed from the cannula 62 and placed in a sterilization tray and the patient placed in a Trendelenburg position so that the apex of the peritoneum is above the end of the cannula 62 within the peritoneum. Up to 1.5 liters of air is infused.

Any air bubbles observed moving up between the guide 10 and the cannula 62 during insufflation indicate that the distal tip 86 of the cannula 62 is touching the viscera. This indicates that the infusion of air is blocked so that the air is forced back up between the cannula 62 and guide 10. Withdrawing the cannula 62 between about 1 and about 2 mm will help remedy that situation, as will compressing the guide onto the cannula 62 while insufflating. After enough air has been infused, the tubing is disconnected from the cannula 62.

The scope 80 is reinserted and locked into the cannula 62. If the tip of the scope 80 rests upon the visceral peritoneum, a highly reflective surface that moves with inspiration will be observed. The scope 80 should be retracted millimeter by millimeter while inspecting the images. When the tip 84 enters the edge of the airspace, the surfaces of the bowel and omentum will be seen several centimeters from scope 80.

The cannula 62 is advanced until hub 17 of the cannula 62 meets the skin surface, or until the tip of the scope 80 reaches the distant peritoneal surface. The scope 80 is removed from the cannula 62 and returned to the sterilization tray. The assembly 58 is rotated so that tab 28 of guide 10 is next to the patient's abdomen and the slot 20 is facing up. The tab 28 is firmly gripped, in one preferred embodiment by hand or by attaching a hemostat to the tab 28 at a point between about 1 to about 2 mm from the hub 17 of the cannula 62. At this point, clip 72 or any other securing device including restraining tape, should be removed.

Figure 22:
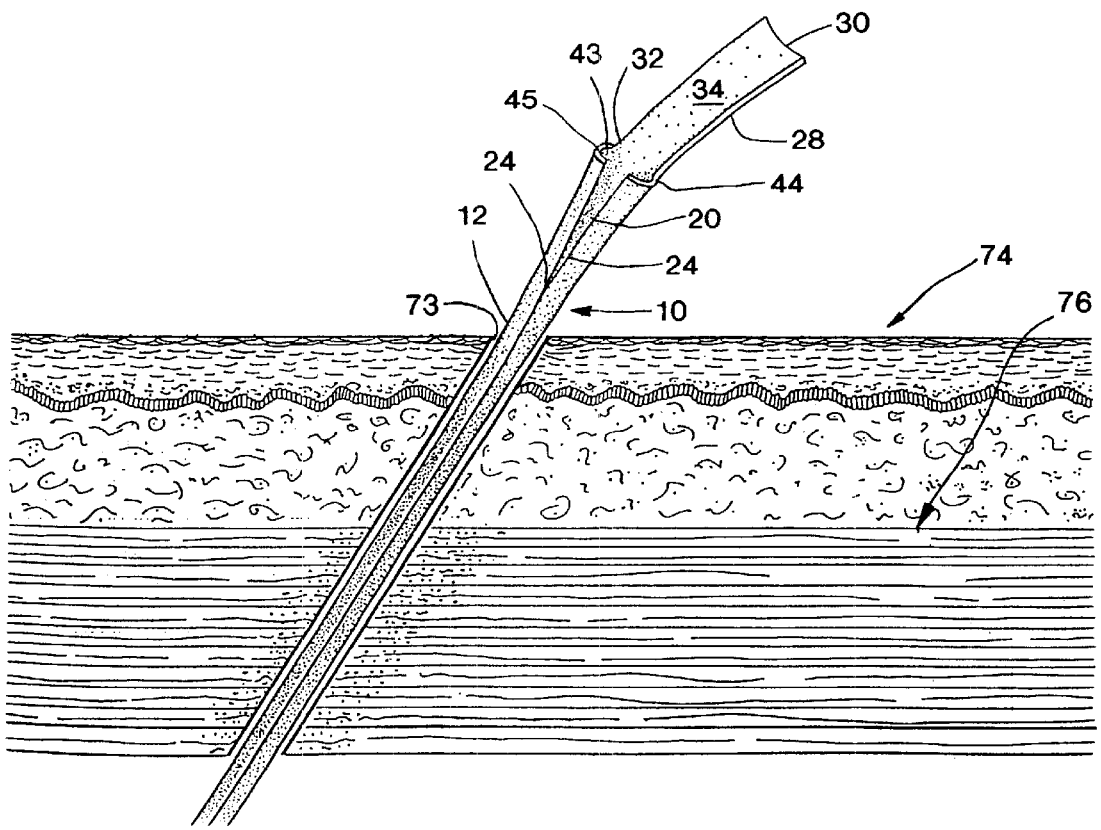
FIG. 22 is a schematic representation of the guide implanted in the patient.

The cannula 62 is removed by twisting it gently back and forth while pulling up to dislodge the tip 46 of the guide 10 from the cannula 62. If there is resistance and the tip 46 does not release immediately, the cannula 62 is reinserted and twisted while pulling upward on the cannula 62 until only guide 10 remains as shown in FIG. 22. The diameter of the guide 10 and the "hole", i.e., entry point 73, within the musculature 76 is too small to insert the standard peritoneal dialysis catheter and thus needs to be dilated.

Figure 24:
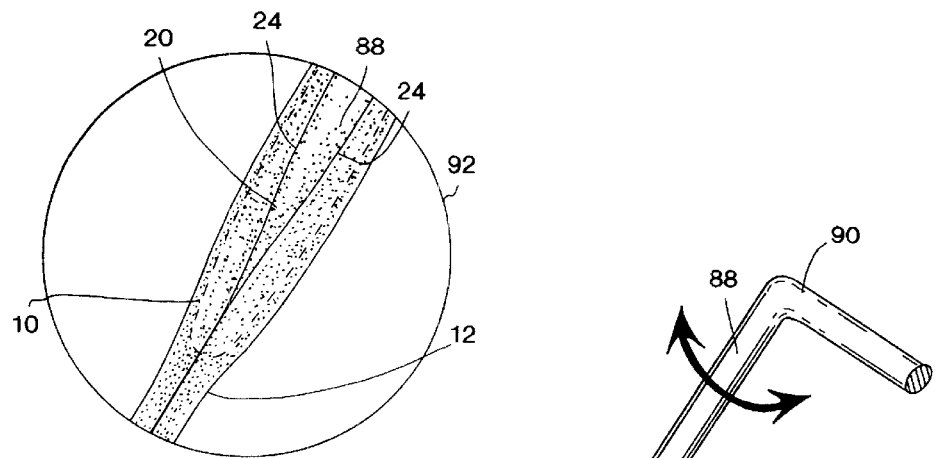
FIG. 24 is an enlarged partial view of the dilator and guide of FIG. 23.
Figure 23:
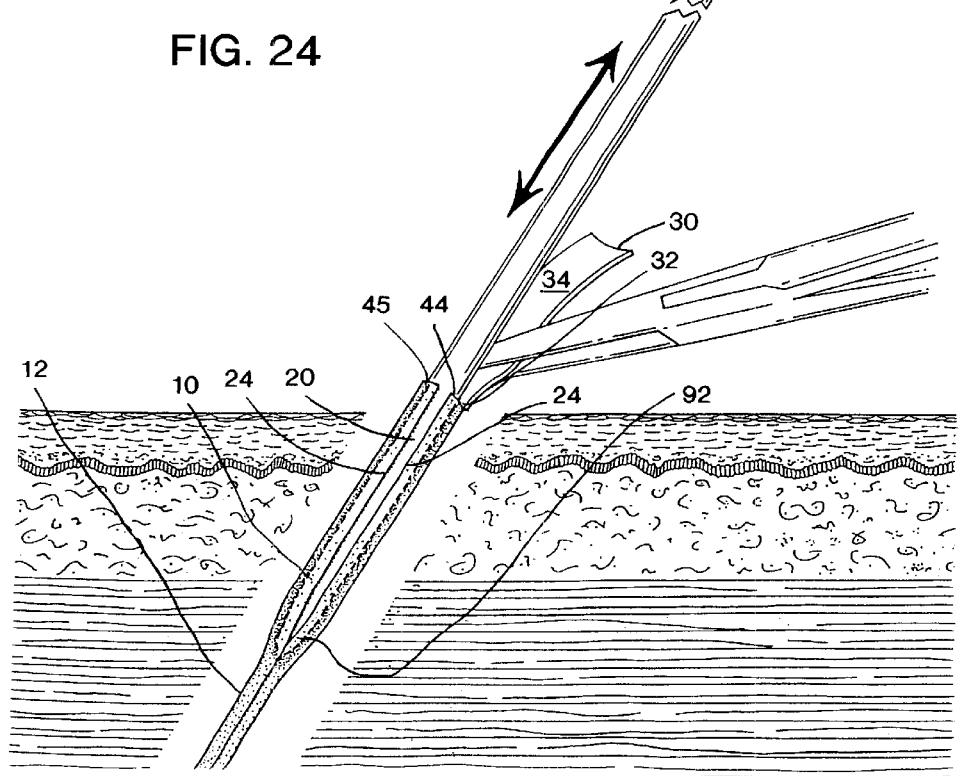
FIG. 23 is a schematic representation of the dilator used with the guide.

While the guide 10 is secured by hand or a hemostat, a small dilator 88, shown in FIGS. 23 and 24 having a handle 90 and distal tip 92, is wet with saline. The dilator 88 is inserted into the guide 10 and slowly advanced with a slight twisting motion as passes through the musculature 76 and the peritoneum. Advancement of the dilator 88 is stopped as resistance decreases as it passes through the abdominal wall. The dilator 88 is moved in and out of the musculature 76 several times until resistance is minimal.

Before the catheter 94 is implanted, it must be immersed in sterile saline. While in the saline, the catheter's cuff portions 96 are squeezed and rotated several times to eliminate any air trapped within them since air inhibits the ingrowth of fibrous tissue. In one preferred embodiment, cuff portion 96 is comprised of proximal and distal cuffs 96 and 98 respectively. Sterile saline is also injected through the catheter 94 via a syringe.

It is important to orient the catheter 94 before a catheter stylette is inserted. Improperly oriented catheters may rotate, kink, migrate or fail. To orient the catheter 94, it is laid, in its normal predetermined position, flat on the patient's abdomen. It is important that during the actual insertion step the elongated portion 102 between the cuff portions 96 remains at the same relative position throughout the entire process. If the catheter 94 is not positioned properly, it may rotate, kink, flip, migrate, leak, all of the above, or even fail. A catheter stylette is wet and inserted into the pre-soaked catheter 94. This makes the catheter 94 sufficiently rigid to insert through the guide 10. The stylette should stop within about 0.5 to about 1 cm of the catheter tip 104.

Figure 26:
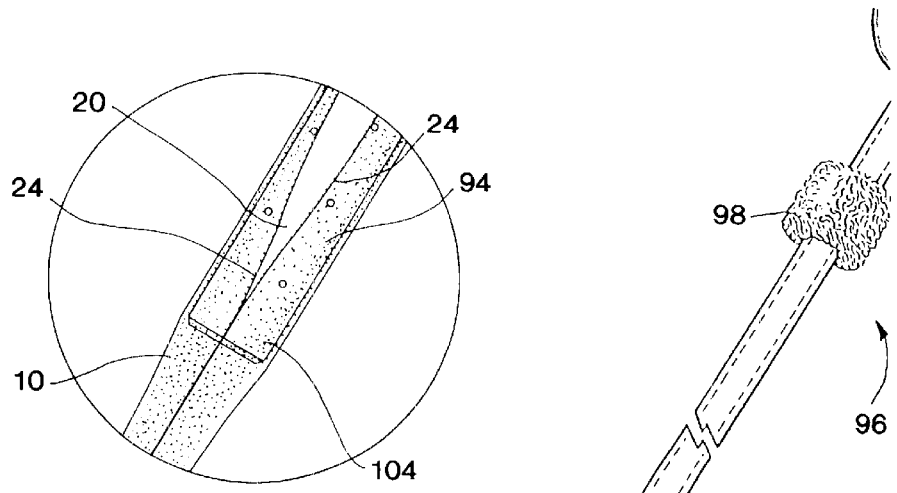
FIG. 26 is an enlarged partial view of the flexible catheter and guide of FIG. 25.
Figure 25:
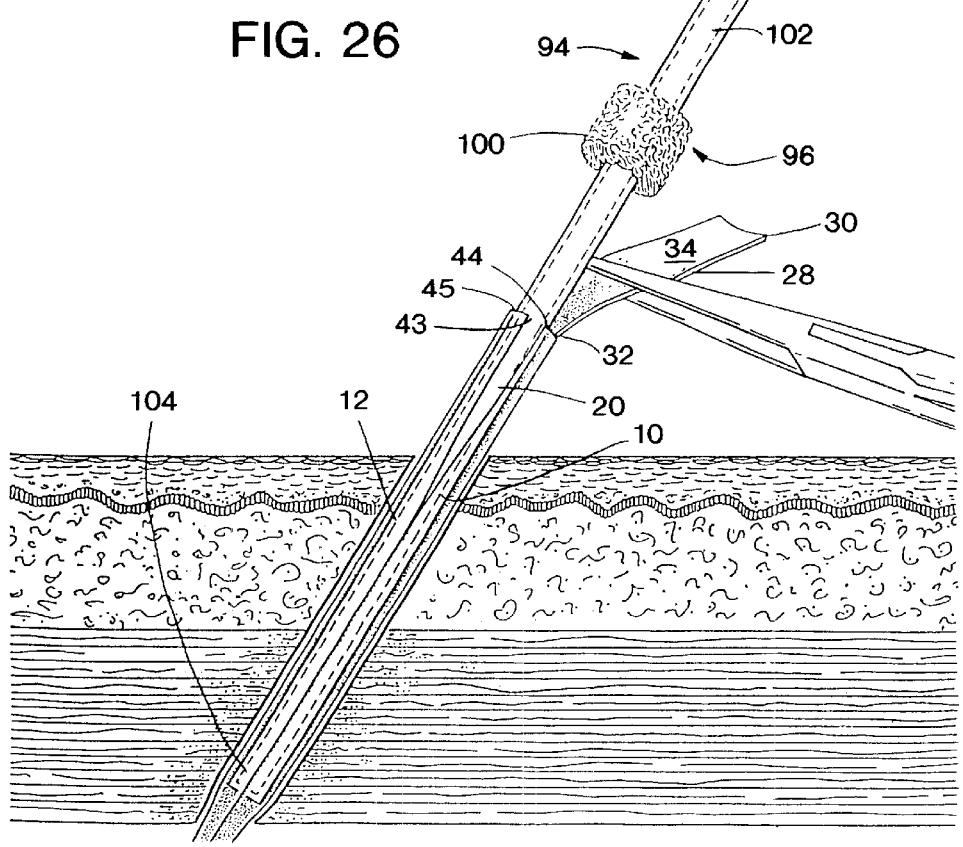
FIG. 25 is a schematic representation of the flexible catheter inserted through the guide of FIG. 16.

With the wetted stylette in the catheter 94, the catheter 94 is grasped by the surgeon about 12 to about 15 cm (5 to about 6 inches) from the distal end and inserted firmly into the guide 10 as shown in FIGS. 25 and 26. The tip 104 of catheter 94 is watched to ascertain that it is within the guide 10. The catheter 94 is steadily advanced about 2 to about 3 cm at a time until the distal cuff 100 reaches the anterior sheath of the rectus muscle.

Figure 27:
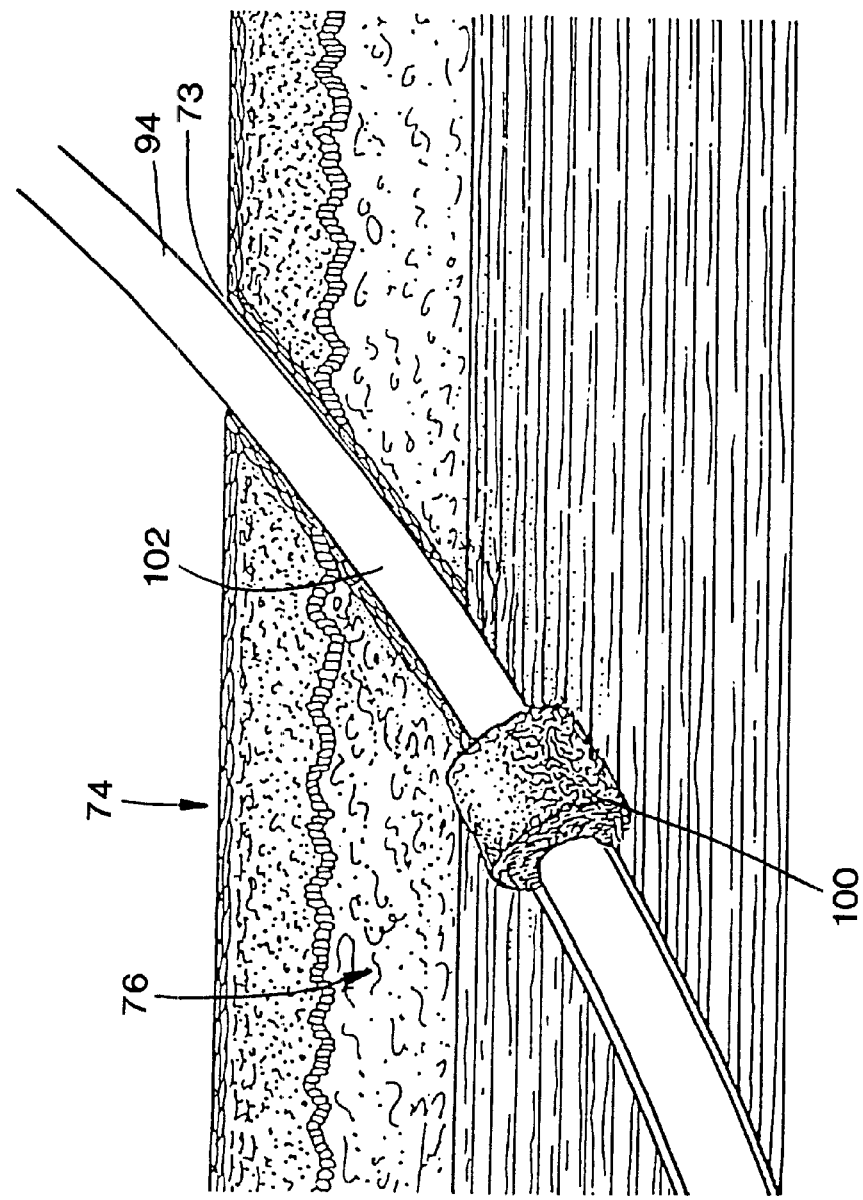
FIG. 27 is a schematic representation of the final implanted position of the flexible catheter of FIGS. 25 and 26.

During insertion, the catheter 94 is stopped due to the fact that the dilation diameter of the musculature matches that of the catheter 94, but the cuff portion 96 diameter is larger. In some situations, the final position of catheter 94 can be reached by continuing to advance the catheter 94, about 1 cm, so that the cuff portion 94 will dilate, reaching its own final position within the muscle. However, the depth and position of the cuff portion 94 can be difficult to control. For maximum stability of the catheter 94, the distal cuff 100 should be placed within the rectus muscle. (FIG. 27) One secure way to position the distal cuff 100 within the rectus muscle is to use a cuff implantor. The catheter stylette remains in the catheter 94 which is still inside the guide 10. The implantor "snaps" onto the catheter 94 between the distal and proximal cuffs 100 and 98 and is slid down the catheter 94 inside the guide 10 until the leading edge of the implantor touches the distal cuff 100. The implantor is carefully advanced about 1 cm, pushing cuff 100 before it into the rectus muscle. Preferably a "finger" on the implantor inhibits the implantor and, therefore, the cuff 100 itself from going through the rectus muscle. When distal cuff 100 is properly positioned, the implantor is removed as shown in FIG. 27.

In this location, fibroblasts can and will grow rapidly into the distal cuff 100. When the catheter 94 is anchored within the rectus by the cuff 100, the risks of peri-catheter leaks, peri-catheter hernias and catheter extrusion are greatly reduced.

An alternative method to position the distal cuff 100 within the muscle is to take a second hemostat, open the tips, and slide the tips within the guide 10 to the cuff 100. Distal cuff 100 is firmly and gently advanced about 1 cm into the muscle until properly positioned.

With the stylette still within the catheter 94, and holding the catheter 94 securely so as not to dislodge the distal cuff 100, the surgeon pulls up on tab 28, preferably by hand but a hemostat may be employed, to remove guide 10. A sure grip is assured as tab 28 has at least one surface, or portion thereof, that is textured. Slot 20 in guide 10 allows it to slide around the catheter 94 and the distal cuff 100 without dislodging either one. The catheter stylette can now be removed. A finger is inserted through the primary incision to confirm that the deep cuff is within the musculature.

While a particular embodiment of the present invention has been shown and described, it will be appreciated by those skilled in the art that changes and modifications may be made hereto without departing from the invention in its broadest aspects and as set forth in the following claims.

I claim:

1. A surgical implement guide sized for insertion into and compatible with tissue, and comprising:
    a hollow shaft of flexible material and with memory to return to a predetermined configuration, the shaft defining a central passageway of variable inside diameter and terminating in an access opening, the shaft defining a slot having opposing sides that can slidably pass one over the other to vary the inside diameter of the central passageway;
    a tip opposite said access opening; and
    an axially elongated tab member integral with said shaft, having a width less than the outer diameter of said shaft and positioned adjacent to the access opening.

2. The guide of claim 1 wherein said passageway extends axially along the entire length of said shaft.

3. The guide of claim 1 wherein said shaft provides for the introduction of a surgical instrument into the tissue.

4. The guide of claim 3 wherein said shaft accommodates different sized implements.

5. The guide of claim 1 wherein said elongated tab member has a width substantially equal to an outer circumference of said shaft.

6. The guide of claim 1 wherein said elongated tab member has a width less than the outer circumference of said shaft.

7. The guide of claim 6 wherein said elongated tab member is substantially flat in relation to said shaft.

8. The guide of claim 1 wherein said elongated tab member is substantially rectangular in shape.

9. The guide of claim 1 wherein said elongated tab member is substantially angled in shape.

10. The guide of claim 1 wherein said elongated tab member has at least one smooth surface.

11. The guide of claim 1 wherein said tip is in fluid communication with said central passageway.

12. The guide of claim 11 wherein said tip has an outer diameter substantially equal to an outer diameter of said shaft.

13. The guide of claim 11 wherein said tip has an outer diameter less than an outer diameter of said shaft.

14. The guide of claim 1 wherein said tip is pointed.

15. The guide of claim 1 wherein said tip is blunted.

16. The guide of claim 9 wherein said tip is round.

17. The guide of claim 1 wherein said shaft has an outer diameter that is substantially the same over the entire length of said shaft.

18. The guide of claim 17 wherein said shaft is substantially cylindrical in shape.

19. The guide of claim 18 wherein said shaft is substantially conical in shape.

20. The guide of claim 19 wherein said shaft is truncated.

21. The guide of claim 1 wherein said shaft has an outer diameter that varies over the length of said shaft.

22. The guide of claim 1 wherein said shaft has at least one notch formed therein, whereby said notch positions the guide relative to other surgical tools.

23. A surgical implement guide sized for insertion into and compatible with tissue comprising:
    a hollow shaft formed of a flexible material with memory to return to a predetermined configuration, said shaft having distal and proximal ends and defining a central passageway of variable inside diameter and terminating in an access opening at said proximal end, said shaft defining a slot having opposing sides that can slidably pass one over the other to vary the inside diameter of the central passageway;
    an axially elongated tab member having a width less than the outer diameter of said shaft, at least one textured surface extending from said proximal end and integral thereto, and adjacent to said access opening; and
    a tip extending from said distal end and integral thereto and in fluid communication with said central passageway.

24. The guide of claim 23 wherein said tab member is substantially flat in relation to said shaft.

25. The guide of claim 23 wherein said tab member is substantially rectangular in shape.

26. The guide of claim 23 wherein said tab member has at least one smooth surface.

27. The guide of claim 23 wherein said tip has an outer diameter substantially equal to an outer diameter of said shaft, whereby said tip and said shaft are substantially cylindrical in shape.

28. The guide of claim 23 wherein said tip has an outer diameter smaller than an outer diameter of said shaft.

29. The guide of claim 28 wherein said tip is pointed.

30. The guide of claim 28 wherein said outer diameter of said shaft is substantially the same over the entire length of said shaft, whereby said shaft is substantially cylindrical in shape.

31. The guide of claim 28 wherein said outer diameter of said shaft varies over the length of said shaft, whereby said shaft is substantially conical in shape.

32. The guide of claim 28 wherein said shaft has at least one notch formed therein, whereby said notch positions the guide relative to a surgical tool received by the guide.

33. A surgical implement assembly which includes a trocar and sized for insertion into and compatible with tissue comprising:
- a hollow guide surrounding the trocar, said guide having a shaft portion formed of a flexible material with memory to return to predetermined configuration, the shaft portion defining a central passageway of variable inside diameter and terminating in an access opening, and the shaft portion defining a slot having opposing sides that can slidably pass one over the other to vary the inside diameter of the central passageway;
- an axially elongated tab extending from and integral to a proximal end thereof and adjacent said access opening, said elongated tab having a width less than the outer diameter of said shaft portion, at least one textured surface, and acting as a handle; and
- a tip portion extending from and integral to a distal end thereof and in fluid communication with said central passageway.

34. The assembly of claim 33 where said guide is operably connected to said trocar by a clip in the proximal end region of said shaft portion, whereby said clip compressedly urges said guide to said trocar.

35. The assembly of claim 34 wherein said proximal end of said shaft portion further includes a groove formed therein for receiving said clip.

36. The assembly of claim 33 wherein said guide is operably connected to said trocar by an adhesive formed on an inner surface of said guide proximate said proximal end, whereby said adhesive removably bonds said guide to said trocar.

37. The assembly of claim 33 wherein said guide is operably connected to said cannula by removably joining said guide to said trocar by a heat bond.

38. The assembly of claim 33 wherein said tab is substantially flat in relation to said shaft.

39. The assembly of claim 33 wherein said tab is substantially rectangular in shape.

40. The assembly of claim 33 wherein said tip portion has an outer diameter substantially equal to an outer diameter of said shaft portion.

41. The assembly of claim 33 wherein said tip portion has an outer diameter smaller than an outer diameter of said shaft.

42. The assembly of claim 41 wherein said tip portion is pointed.

43. The assembly of claim 41 wherein said tip portion is blunted.

44. The assembly of claim 41 wherein said tip is round.

45. The assembly of claim 41 wherein said shaft portion has an outer diameter that is substantially the same over the entire length of said shaft.

46. The assembly of claim 45 wherein said shaft portion is substantially cylindrical in shape.

47. The assembly of claim 41 wherein said shaft portion has outer diameter that varies over the length of said shaft.

48. The assembly of claim 47 wherein said shaft portion is substantially conical in shape.

\* \* \* \* \*